US006403071B1

(12) United States Patent
Scavone et al.

(10) Patent No.: US 6,403,071 B1
(45) Date of Patent: *Jun. 11, 2002

(54) ANHYDROUS ANTIPERSPIRANT AND DEODORANT COMPOSITIONS CONTAINING SOLID D-PANTOTHENATE SALTS

(75) Inventors: Timothy Alan Scavone, Loveland; Benjamin Scott Schlagheck, Lebanon, both of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/799,367

(22) Filed: Mar. 5, 2001

(51) Int. Cl.$^7$ .................................................. A61K 7/32
(52) U.S. Cl. ............................ 424/65; 424/66; 424/68; 424/400; 424/401
(58) Field of Search .............................. 424/65, 66, 68, 424/400, 401

(56) References Cited

U.S. PATENT DOCUMENTS

| | | |
|---|---|---|
| 2,780,645 A | 2/1957 | Wehrmeister |
| 2,845,456 A | 7/1958 | Kagan |
| 2,935,528 A | 5/1960 | Kapp et al. |
| 3,275,643 A | 9/1966 | Lubowe |
| 4,970,220 A | 11/1990 | Chaussee |
| 5,955,065 A | 9/1999 | Thong et al. |

FOREIGN PATENT DOCUMENTS

| | | |
|---|---|---|
| JP | 12-186014 | 7/2000 |
| WO | WO00/47169 | 8/2000 |
| WO | WO00/47170 | 8/2000 |
| WO | WO00/47171 | 8/2000 |
| WO | WO00/47182 | 8/2000 |

OTHER PUBLICATIONS

Susan Budavari, Editor et al., "The Merck Index An Encyclopedia of Chemicals, Drugs, and Biologicals", 1989, pp. 255 and 1110, Eleventh Edition, Merck & Co., Inc., Rahway, NJ, USA.

*Primary Examiner*—Shelley A. Dodson
(74) *Attorney, Agent, or Firm*—William J. Winter

(57) ABSTRACT

Disclosed are anhydrous antiperspirant and deodorant compositions comprising from about 0.1% to about 30% by weight of an underarm active (antiperspirant and/or deodorant active); from about 0.01% to about 10% by weight of a solid, water-soluble, d-pantothenate salt such as calcium pantothenate; from about 0.1% to about 40% by weight of a suspending agent; and from about 10% to about 99% by weight of an anhydrous carrier liquid. Also disclosed are methods of controlling perspiration wetness and/or odor through the topical application to the underarm, especially shaven underarms, of an underarm active and a solid pantothenate salt. The anhydrous compositions are mild to the skin and can help sooth or heal skin irritated or damaged underarm skin, especially when such irritation and damage is the result of occasional or routine shaving of the underarm.

19 Claims, No Drawings

ANHYDROUS ANTIPERSPIRANT AND DEODORANT COMPOSITIONS CONTAINING SOLID D-PANTOTHENATE SALTS

TECHNICAL FIELD

The present invention relates to anhydrous antiperspirant and deodorant compositions that contain a solid d-pantothenate salt in an anhydrous matrix. The composition provides skin health benefits such as improved wound healing and reduced skin irritation.

BACKGROUND OF THE INVENTION

Many different antiperspirant and deodorant products are known for use in controlling or inhibiting underarm perspiration wetness and odor. These products are available in a variety of product forms such as solid sticks, soft solids or creams, roll-on liquids and aerosol or non-aerosol sprays. Most of these products, however, are similar in having a base formula that contains an antiperspirant active such as an aluminum and or zirconium salt, a suspending or thickening agent, and a suitable liquid carrier.

Antiperspirant and deodorant products can be formulated to contain materials to help sooth or minimize irritation of the underarm skin, especially in those consumers that shave their underarms and apply antiperspirant and deodorant products to the shaved area. The shaving process can irritate and damage the underarm skin, and it is for that reason that antiperspirant and deodorant products are occasionally formulated with materials such as aloe, allantoin, and pantothenoic acid and related materials, to minimize or heal such skin irritation and skin damage. It is well known that pantothenic acid and similar other materials can be used as wound healing agents in a variety of personal care products, including antiperspirant and deodorant products.

Pantothenic acid and related materials can be formulated with an aqueous antiperspirant or deodorant active to provide wound healing and skin soothing benefits to the applied area of the skin. Examples of these skin soothing materials include pantothenic acid and pantothenic derivatives and salts such as d-panthenol, dl-panthenol, and pantothenate salts such as calcium pantothenate. The pantothenate salts are especially useful in providing wound healing and skin soothing benefits, even in combination with antiperspirant and deodorant actives. These highly preferred pantothenate salts are formulated into either an anhydrous or aqueous antiperspirant product matrix, wherein the salts are solubilized within the product matrix by water or other solvents. The product matrix containing the solubilized salts is then applied to the desired area of the skin so that the solubilized salts are allowed to spread or flow over the applied surface, thus helping to sooth or heal any irritated areas of the skin within the applied area.

It has now been found that anhydrous antiperspirant and deodorant products can be formulated with pantothenate salts as solid dispersed particulates, and still provide a soothing and healing effect on the underarm area of the skin, especially underarm skin that has been irritated or damaged by shaving. It is believed that the solid pantothenate salts are readily dissolved by the sweat or other moisture on the underarm, thus allowing the solids to dissolve after application. Once the product matrix is applied to the underarm area, the solid pantothenate salts dissolve in the sweat or other moisture on the skin and then flow or spread onto the applied surface of the underarm, thus helping to sooth, heal or mitigate any skin irritation or wounds associated with the underarm, especially skin wounds or irritation caused by shaving the underarm. It is also believed that by delaying dissolution of the pantothenate salts until after product application, that these solid particulates are then less likely than their dissolved counterparts to interact with other materials in the product matrix prior to application, including interaction with aluminum and zirconium antiperspirant actives or deodorant actives in the product matrix prior to application.

It therefore an object of the present invention to provide new anhydrous antiperspirant and deodorant compositions that contain materials to sooth or heal irritated underarm skin, especially underarm skin that has been irritated or damaged by shaving. It is a further object of the present invention to provide such a composition that contains solid pantothenate salts, especially solid calcium pantothenate salts, as dispersed particulates in an anhydrous antiperspirant and deodorant matrix.

SUMMARY OF THE INVENTION

The present invention is directed to anhydrous antiperspirant and deodorant compositions that comprise from about 0.1% to about 30% by weight of an antiperspirant or deodorant active; from about 0.01% to about 10% by weight of a solid, water-soluble, d-pantothenate salt; from about 0.1% to about 40% by weight of a suspending agent; and from about 10% to about 99% by weight of an anhydrous carrier liquid. The anhydrous antiperspirant and deodorant compositions are mild to the skin and provide skin soothing or healing benefits, especially when applied to the underarm after shaving.

It has been found that the d-pantothenate salts can be formulated as solid particulates in an anhydrous antiperspirant or deodorant composition, and still provide excellent skin soothing and healing benefits to the underarm. It is believed that the solid d-pantothenate salts help to minimize ingredient incompatibilities associated with the use of dissolved pantothenate salts in antiperspirant and deodorant products.

DETAILED DESCRIPTION OF THE INVENTION

The anhydrous antiperspirant and deodorant compositions of the present invention comprise as essential components an antiperspirant or deodorant active, a solid d-pantothenate salt, a suspending agent, and an anhydrous liquid carrier. Each of these essential components of the present invention is described hereinafter in more detail.

The term "anhydrous" as used herein means that the antiperspirant and deodorant compositions of the present invention, and the essential or optional components thereof, are substantially free of added or free water. From a formulation standpoint, this means that the anhydrous antiperspirant and deodorant compositions of the present invention preferably contain less than about 5%, more preferably less than about 3%, even more preferably less than about 1%, most preferably zero percent, by weight of free or added water, other than the water of hydration typically associated with any particulate solids prior to formulation.

All melting point values referenced herein, unless otherwise specified, are measured and determined according to well known Differential Scanning Calorimetry (DSC) technique. Examples of DSC technique for determining melting point values of various materials are described in U.S. Pat. No. 5,306,514 (Letton et al.), which description is incorporated herein by reference.

The term "ambient conditions" as used herein refers to surrounding conditions under about one (1) atmosphere of pressure, at about 50% relative humidity, and at about 25° C., unless otherwise specified. All values, amounts and measurements described herein are obtained under ambient conditions unless otherwise specified.

The term "volatile" as used herein refers to those materials that have a measurable vapor pressure at 25° C. Such vapor pressures will typically range from about 0.01 mmHg to about 6 mmHg, more typically from about 0.02 mmHg to about 1.5 mmHg, and have an average boiling point at one (1) atmosphere of pressure (atm) of less than about 250° C., more typically less than about 235° C. at one (1) atm. Conversely, the term "non volatile" refers to those materials that are not "volatile" as defined herein.

The term "skin temperature" as used herein refers to the temperature of the axilla area of the skin, which is generally at or slightly below a typical body temperature of about 37° C.

The term "water-soluble" as used herein refers to those materials, including the water-soluble skin active agent as described herein, that can be dissolved in deionized water at 37° C. under otherwise ambient conditions to form an aqueous solution containing at least 0.1% by weight of the dissolved material, preferably at least about 0.5% by weight of the dissolved material.

The anhydrous antiperspirant and deodorant compositions of the present invention can comprise, consist of, or consist essentially of the essential elements and limitations of the invention described herein, as well as any additional or optional ingredients, components, or limitations known or otherwise effective for use in such compositions.

All percentages, parts and ratios are by weight of the total composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

Antiperspirant Active

The anhydrous antiperspirant and deodorant compositions of the present invention comprise an underarm active suitable for application to human skin. The concentration of the underarm active, which can be either an antiperspirant and or deodorant active, should be sufficient to provide the desired perspiration wetness or odor control from the anhydrous formulation selected.

The anhydrous antiperspirant embodiments of the present invention preferably comprise antiperspirant active at concentrations ranging from about 0.1% to about 30%, more preferably from about 5% to about 30%, by weight of the composition. These weight percentages are calculated on an anhydrous metal salt basis exclusive of water and any complexing agents such as glycine, glycine salts, or other complexing agents. The antiperspirant active can be solubilized or solid, preferably as dispersed solid particulates. The antiperspirant active as formulated in the composition is preferably in the form of dispersed particulate solids having a preferred average particle size or diameter of less than about 100 µm, preferably from about 1 µm to about 40 µm.

The antiperspirant active for use in the anhydrous antiperspirant embodiments of the present invention include any compound, composition or other material having antiperspirant activity. Preferred antiperspirant actives include astringent metallic salts, especially inorganic and organic salts of aluminum, zirconium and zinc, as well as mixtures thereof.

Particularly preferred are aluminum- containing and/or zirconium-containing salts or materials, such as aluminum halides, aluminum chlorohydrate, aluminum hydroxyhalides, zirconyl oxyhalides, zirconyl hydroxyhalides, and mixtures thereof.

Preferred aluminum salts for use in the anhydrous antiperspirant embodiments of the present invention include those which conform to the formula:

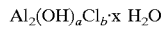

$$Al_2(OH)_aCl_b \cdot x\, H_2O$$

wherein a is from about 2 to about 5; the sum of a and b is about 6; x is from about 1 to about 6; and wherein a, b, and x may have non-integer values. Particularly preferred are the aluminum chlorohydroxides referred to as "5/6 basic chlorohydroxide", wherein a=5, and "2/3 basic chlorohydroxide", wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, all of which are incorporated herein by reference. Mixtures of aluminum salts are described in British Patent Specification 1,347,950, Shin et al., published Feb. 27, 1974, which description is also incorporated herein by reference.

Preferred zirconium salts for use in the anhydrous antiperspirant embodiments of the present invention include those which conform to the formula:

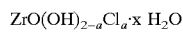

$$ZrO(OH)_{2-a}Cl_a \cdot x\, H_2O$$

wherein a is from about 1.5 to about 1.87; x is from about 1 to about 7; and wherein a and x may both have non-integer values. These zirconium salts are described in Belgian Patent 825,146, Schmitz, issued Aug. 4, 1975, which description is incorporated herein by reference. Particularly preferred zirconium salts are those complexes which additionally contain aluminum and glycine, commonly known as ZAG complexes. These ZAG complexes contain aluminum chlorohydroxide and zirconyl hydroxy chloride conforming to the above described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978, all of which are incorporated herein by reference.

Antiperspirant actives suitable for use in the compositions include aluminum chlorohydrate, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum zirconium trichlorohydrate, aluminum zirconium tetrachlorohydrate, aluminum zirconium pentatchlorohydrate, aluminum zirconium octachlorohydrate, aluminum zirconium trichlorohydrex glycine complex, aluminum zirconium tetrachlorohydrex glycine complex, aluminum zirconium pentachlorohydrex glycine complex, aluminum zirconium octachlorohydrex glycine complex, aluminum chloride, aluminum sulfate buffered, and combinations thereof.

Antimicrobial Deodorant Active

The antiperspirant and deodorant compositions of the present invention can also be formulated with an underarm active in the form of an antimicrobial deodorant material in addition to or in place of the antiperspirant active. Deodorant active concentrations in the compositions can range from about 0.1% to about 30%, preferably from about 0.1% to about 10%, even more preferably from about 0.1% to about 3%, by weight of the composition. These deodorant actives include any known or otherwise safe and effective antimicrobial deodorant active suitable for topical application to human skin, and which is effective in preventing or eliminating malodor associated with perspiration.

Non-limiting examples of preferred antimicrobial deodorant actives for use in the antiperspirant and deodorant compositions of the present invention include cetyltrimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichlorio-2'-hydroxy diphenyl ether (triclosan), 3,4, 4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof. Preferred are triclosan, triclocarban, and combinations thereof.

Other deodorant actives suitable for use herein are described in U.S. Pat. No. 6,013,248 (Luebbe et al.), which descriptions are incorporated herein by reference.

D-Pantothenate Salts

The anhydrous antiperspirant compositions of the present invention comprise a solid particulate that is suspended or otherwise dispersed throughout the compositions, wherein the solid particulate is a water-soluble, d-pantothenate salt that is in solid particulate form within the composition. The solid d-pantothenate salts for use in the antiperspirant and deodorant compositions of the present invention can include any salt of d-pantothenic acid or any salt of d-pantothenic acid derivatives, provided that the d-pantothenate salt is in solid particulate form within the composition.

The concentration of solid d-pantothenate salt ranges from about 0.01% to about 10%, preferably from about 0.05% to about 5%, more preferably from about 0.1% to about 1.0%, by weight of the compositions.

The d-pantothenate salt for use in the anhydrous compositions of the present invention must be in solid particulate form within the composition under ambient conditions, and must also be water-soluble as defined herein. These solid particulates within the composition preferably have an average particle diameter of from about 3 $\mu$m to about 100 $\mu$m, more preferably from about 5 $\mu$m to about 40 $\mu$m.

The d-pantothenate salts may be obtained and used in their pure d-enantomeric form, or may be used as part of a d-1 racemic mixture, although it is believed that most or all of the skin soothing and healing benefits made possible by these materials is derived from the d-enantomer rather than from the relatively inactive 1-enantomer.

Preferred pantothenate salts for use in the anhydrous antiperspirant and deodorant compositions of the present invention include sodium salts, potassium salts, calcium salts, magnesium salts, lithium salts, and combinations thereof. Most preferred is calcium pantothenate.

Suspending Agent

The anhydrous antiperspirant and deodorant compositions of the present invention comprise a solid suspending or thickening agent to help provide the compositions with the desired viscosity, rheology, texture and/or product hardness, or to otherwise help suspend any dispersed solids or liquids within the composition.

The term "suspending agent" as used herein, unless otherwise specified, means any material known or otherwise effective in providing suspending, gelling, viscosifying, solidifying and/or thickening properties to the composition or which otherwise provide structure to the final product form. These suspending agents include gelling agents, and polymeric or nonpolymeric or inorganic thickening or viscosifying agents. Such materials will typically be solids under ambient conditions and include organic solids, silicone solids, crystalline or other gellants, inorganic particulates such as clays or silicas, or combinations thereof.

The concentration and type of suspending agent selected for use in the antiperspirant and deodorant compositions will vary depending upon the desired product hardness, rheology, formulation (e.g., antiperspirant formulation or deodorant formulation) and/or other related product characteristics. For most suspending agents suitable for use herein, the total suspending agent concentration ranges from about 0.1% to about 40%, more typically from about 0.1% to about 35%, by weight of the composition. Suspending agent concentrations will tend to be lower for liquid embodiments (e.g., aerosols, roll-ons, etc) and higher for semi-solid (e.g., soft solids or creams) or solid stick embodiments.

Non limiting examples of suitable suspending agents include hydrogenated castor oil (e.g., Castorwax MP80, Castor Wax, etc.), fatty alcohols (e.g., stearyl alcohol), solid paraffins, triglycerides and other similar solid suspending esters or other microcrystalline waxes, silicone and modified silicone waxes. Non limiting examples of optional suspending agents suitable for use herein are described in U.S. Pat. No. 5,976,514 (Guskey et al.), U.S. Pat. No. 5,891,424 (Bretzler et al.), which descriptions are incorporated herein by reference.

Other suitable suspending agents include silicone elastomers at concentrations ranging from about 0.1% to about 10%, by weight of the composition. Non-limiting examples of such silicone elastomer materials suitable for use as a suspending agent herein are described in U.S. Pat. No. 5,654,362 (Schulz, Jr. et al.); U.S. Pat. No. 6,060,546 (Powell et al.) and U.S. Pat. No. 5,919,437 (Lee et al.), which descriptions are incorporated herein by reference.

Non-limiting examples of suitable suspending agents for use in deodorant embodiments of the present invention include fatty acid salts such as sodium stearate and other similar materials as described in U.S. Pat. No. 6,013,248 (Luebbe et al.), which description is incorporated herein by reference.

Anhydrous Carrier Liquid

The anhydrous antiperspirant and deodorant compositions of the present invention comprise an anhydrous carrier liquid at concentrations ranging from about 10% to about 99%, preferably from about 20% to about 70%, by weight of the composition. Such concentrations will vary depending upon variables such as product form, desired product hardness, selection of other ingredients in the composition, and so forth. The anhydrous carrier liquid for use in the composition can be any anhydrous liquid that is known for use in personal care applications or is otherwise suitable for topical application to the skin.

The anhydrous carrier liquid preferably comprises a volatile silicone liquid, which may include cyclic, linear and/or branched chain silicones. The concentration of volatile silicone in the antiperspirant composition of the present invention preferably ranges from about 5% to about 80%, preferably from about 20% to about 60%, more preferably from about 30% to about 60%, by weight of the composition. The volatile silicone is preferably a cyclic silicone having from about 3 to about 7, more preferably from about 5 to about 6, silicon atoms. Most preferred are those that conform to the formula:

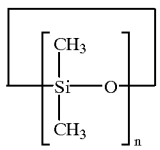

wherein n is from about 3 to about 7, preferably from about 5 to about 6, most preferably 5. These volatile cyclic silicones generally have a viscosity of less than about 10 centistokes. Suitable volatile silicones for use herein include, but are not limited to, Cyclomethicone D5 (commercially available from G. E. Silicones); Dow Corning 344, and Dow Corning 345 (commercially available from Dow Corning Corp.); and GE 7207, GE 7158 and Silicone Fluids SF-1202 and SF-1173 (available from General Electric Co.). Non limiting examples of suitable volatile silicones are described in Todd et al., "Volatile Silicone Fluids for Cosmetics", Cosmetics and Toiletries, 91:27–32 (1976), which descriptions are incorporated herein by reference.

The anhydrous liquid carrier may comprise a non-volatile silicone liquid, preferred concentrations of which range from about 1% to about 35%, more preferably from about 5% to about 30%, by weight of the composition. The non volatile silicone carrier is preferably a liquid at or below human skin temperature, or otherwise in liquid form within the anhydrous antiperspirant composition during or shortly after topical application. Preferred are those nonvolatile liquid silicones that conform to either of the formulas:

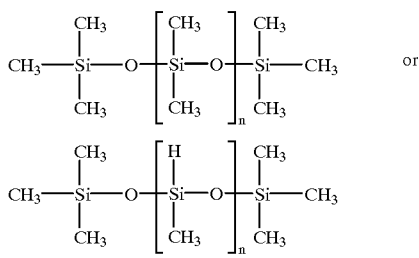

wherein n is sufficiently large to provide a viscosity of up to about 100,000 centistokes, preferably less than about 500 centistoke, more preferably from 10 centistoke to about 200 centistoke, even more preferably from 10 centistoke to about 50 centistoke, as measured under ambient conditions. Specific non limiting examples of suitable non volatile, linear, silicone carriers include Dow Corning 200, hexamethyldisiloxane, Dow Corning 225, Down Corning 1732, Dow Corning 5732, Dow Corning 5750 (available from Dow Corning Corp.); and SF-96, SF-1066 and SF18 (350) Silicone Fluids (available from G.E. Silicones).

Many other carrier liquids known for use in personal care products can be used in the antiperspirant compositions, alone or in combination with the carrier liquids described in more detail herein. Many such other carrier liquids are disclosed in U.S. Pat. No. 6,013,248 (Luebbe et al.) and U.S. Pat. No. 5,968,489 (Swaile et al.), which descriptions are incorporated herein by reference.

Optional Ingredients

The anhydrous antiperspirant and deodorant compositions of the present invention may further comprise any optional ingredient that is known for use in antiperspirants and deodorant products or other personal care products, or which is otherwise suitable for topical application to human skin.

Non limiting examples of optional ingredients include dyes or colorants, emulsifiers, perfumes, propellants, deodorant perfumes, preservatives, vitamins, non-vitamin nutrients, emollients, coupling agents or other solvents, surfactants, processing aides such as viscosity modifiers, wash-off aids, and so forth. Examples of such optional materials are described in U.S. Pat. No. 4,049,792 (Elsnau); U.S. Pat. No. 5,019,375 (Tanner et al.); and U.S. Pat. No. 5,429,816 (Hofrichter et al.); which descriptions are incorporated herein by reference.

Methods of Manufacture

The anhydrous antiperspirant and deodorant compositions of the present invention may be prepared by any known or otherwise effective technique suitable for formulating the desired antiperspirant or deodorant product form.

Antiperspirant solid and semi-solid embodiments of present invention can be formulated, for example, by mixing volatile and nonvolatile silicone carrier liquids (or any other desired anhydrous carrier liquid) under ambient conditions, or under conditions sufficient to render the admixture fluid or liquid, and then adding any suspending agents to the mixture and heating the resulting mixture sufficiently to liquefy the added suspending agents, e.g., approximately 85° C. for many wax solids, and form a single phase liquid. Antiperspirant active and other water-soluble solids (e.g. solid pantothenate salts) are then typically added to and dispersed throughout the heated, single-phase liquid before allowing the resulting combination to cool to approximately 78° C., at which point perfumes and similar other materials (if any) are mixed into the combination, which is then cooled to just above the solidification point of the suspending agent (e.g., typically about 60° C.) and then poured into dispensing packages and allowed to solidify under ambient conditions.

Antiperspirant liquid embodiments of the present invention can be formulated, for example, by combining an anhydrous carrier liquid with a suitable suspending agent and activator for the suspending agent and allowing the combination to thicken to the desired viscosity before adding the antiperspirant active and other water-soluble solids with agitation. The resulting mixture is subjected to shear in a suitable homogenizer to achieve the desired concentrate viscosity. For aerosol liquid embodiments, the resulting liquid is then packaged into aerosol containers with an appropriate propellant in a concentrate to propellant ratio suitable for the propellant system selected.

Other suitable methods of making antiperspirant compositions are known and described in the antiperspirant art, and can be used to make the antiperspirant compositions of the present inventions. For solid antiperspirant embodiments, such methods include those described in U.S. Pat. No. 4,822,603 (Farris et al.) and U.S. Pat. No. 4,985,238 (Tanner et al.). For aerosol antiperspirant embodiments, such methods include those described in U.S. Pat. No. 6,136,303 (Ruebusch et al.); U.S. Pat. No. 4,904,463 (Johnson et al.) and U.S. Pat. No. 4,840,786 (Johnson et al.) For soft solid or cream embodiments, such methods are described in U.S. Pat. No. 5,902,571 (Putman et al.) and U.S. Pat. No. 5,902,570 (Bretzler et al.). All such method descriptions in the above-identified patent publications are incorporated herein by reference.

Suitable methods of making deodorant embodiments of the present invention are described, for example, in U.S. Pat. No. 6,013,248 (Luebbe et al.) and U.S. Pat. No. 5,902,572 (Luebbe et al.), which descriptions are incorporated herein by reference.

Preferred Manufacturing Method

The anhydrous antiperspirant and deodorant compositions of the present invention are preferably manufactured by subjecting the composition to a milling step to reduce or eliminate relatively large solid agglomerates that can form when the solid pantothenate salts are combined with an antiperspirant or deodorant active in solid particulate form.

It has also been found that the solid pantothenate salts tends to agglomerate with any solid antiperspirant or deodorant active, especially antiperspirant active, to form undesirably large agglomerated solids within the composition. It has also been found that by milling the intermediate formulation prior to pouring the formulations into packages to cool, that the agglomerates can be reduced or eliminated, thus further improving the application cosmetics of the anhydrous antiperspirant and deodorant compositions.

More specifically, the preferred manufacturing method of the present invention comprises the steps of:
(a) preparing an intermediate composition by mixing together the following components:
  (i) from about 0.1% to about 30% by weight of an antiperspirant or deodorant active;
  (ii) from about 0.01% to about 10% by weight of a solid, water-soluble, pantothenate salt;
  (iii) from about 0.1% to about 40% by weight of a suspending agent; and
  (iv) from about 10% to about 99% by weight of an anhydrous carrier liquid; and
(b) heating the intermediate composition to above the melting point of the suspending agent to form a liquid intermediate composition containing solid antiperspirant active and solid, water-soluble, pantothenate salt, and solid aggregates thereof;
(c) milling the liquid intermediate composition for a period of time sufficient to reduce the average particle diameter of the solid aggregates to less than 50 μm; and then
(d) pouring the milled liquid intermediate into a dispensing package and allowing the packaged composition to cool to ambient temperatures, to form an anhydrous antiperspirant and deodorant composition.

The milling step as referred to herein is any process wherein a shear force is applied that effectively breaks up or reduces any agglomeration of particles and disperses the particles throughout the composition. Non limiting examples of such milling or high shearing mixing processes include colloid milling, high pressure homogenization. The average particle diameter of the solid aggregates after the milling step can be measured or otherwise determined by polarized light microscopy methods well known in the various chemical arts.

Method of Use

The anhydrous antiperspirant and deodorant compositions of the present invention may be applied topically to the axilla or other area of the skin in an amount effective to treat or reduce perspiration wetness and or malodor. The composition is preferably applied in an amount ranging from about 0.1 gram to about 20 grams, more preferably from about 0.1 gram to about 10 grams, even more preferably from about 0.1 gram to about 1 gram, to the desired area of the skin. The compositions are preferably applied one to two times daily, preferably once daily, to achieve effective antiperspirant and malodor control.

The anhydrous antiperspirant and deodorant compositions of the present invention can be formulated in a variety of product forms and then applied to the axilla or other area of the skin in the manner described herein, such variety product forms including solids (e.g., sticks), semi-solids (e.g., lotions, creams, soft solids), or liquids (e.g. aerosols, non-aerosol sprays, roll-ons, porous dome liquids).

EXAMPLES

The following non-limiting examples described in Tables 1–5 illustrate specific embodiments of the anhydrous antiperspirant and deodorant compositions of the present invention, including methods of manufacture and use. Each of the exemplified compositions is applied topically to the axilla area of the skin, in accordance with the methods of use described herein, including the application to shaved underarms. The applied compositions are mild to the skin and help heal or sooth irritated underarm skin, including underarms skin that has been shaven.

All exemplified amounts are weight percentages based upon the total weight of the antiperspirant stick composition, unless otherwise specified.

Examples 1–3

Antiperspirant Soft Solids/Creams, Wax Sticks, Low Residue Sticks

The Tables 1–3 examples are each prepared as follows. First, the gellants (fully hydrogenated HEAR and C18–C36 acid triglyceride) are dissolved into the silicone liquids, cyclopentasiloxane and dimethicone, by heating the gellants and silicone materials together while stirring on an IKA stir plate to 85° C. The solid antiperspirant active is then added slowly with agitation to the heated mixture, and once added, the resulting mixture is allowed to reheat to 85° C. At this point the water soluble solids (e.g., niacinamide, calcium pantothenate) are added along with the tocopherol acetate. The mixture is milled at 4 on the speed setting using an IKA brand T 25 Ultra-Turrax disperser using the S 25 N—25F attachment. The product is milled for a period of time sufficient to reduce and break up any agglomerates of solid water-soluble solids and or solid antiperspirant active. To measure when sufficient milling has occurred, a small sample of milled product is withdrawn from the hot mixture on a metal spatula and examined under a polarizing microscope. Product is milled until no visible agglomerates greater than 10 microns of water-soluble solids and or antiperspirant active are evident. Once milling is completed, then the product is cooled and poured at approximately 60° C. into antiperspirant containers, where it is allowed to cool to ambient temperatures to the desired product form.

TABLE 1

Antiperspirant Soft Solids/Creams

| Ingredients | Example 1.1 | Example 1.2 | Example 1.3 | Example 1.4 |
| --- | --- | --- | --- | --- |
| Al Zr Trichlorohydrex Glycinate (solid) | 25.25 | 25.25 | 25.25 | 25.25 |
| Dimethicone (10 cs) | 5.00 | 5.00 | 5.00 | 5.00 |
| Fully Hydrogenated High Erucic | 5.00 | 5.00 | 5.00 | 5.00 |

TABLE 1-continued

Antiperspirant Soft Solids/Creams

| Ingredients | Example 1.1 | Example 1.2 | Example 1.3 | Example 1.4 |
|---|---|---|---|---|
| Acid Rapeseed oil (HEAR oil) | | | | |
| Niacinamide (solid) | 3.50 | 3.50 | 0 | 7.00 |
| C-18-36 Acid Triglyceride | 1.25 | 1.25 | 1.25 | 1.25 |
| Syncrowax HGLC | | | | |
| Perfume | 0.75 | 0.75 | 0.75 | 0.75 |
| Calcium Pantothenate (solid) | 0.50 | 0.50 | 3.50 | 1.00 |
| Tocopherol Acetate | 0.50 | 0 | 0 | 0 |
| Cyclopentasiloxane | QS | QS | QS | QS |
| Total | 100.00 | 100.00 | 100.00 | 100.00 |

TABLE 2

Antiperspirant Wax Sticks (Solid)

| Ingredients | Example 2.1 | Example 2.2 | Example 2.3 | Example 2.4 |
|---|---|---|---|---|
| Al Zr Trichlorohydrex Glycinate (solid) | 20.00 | 20.00 | 20.00 | 20.00 |
| Stearyl Alcohol | 11.00 | 11.00 | 11.00 | 11.00 |
| Talc, USP Grade | 6.50 | 7.00 | 7.50 | 3.00 |
| Niacinamide (solid) | 3.50 | 3.50 | 0 | 7.00 |
| Dimethicone (50 cs) | 3.00 | 5.00 | 5.00 | 5.00 |
| Castor Wax | 2.90 | 5.00 | 5.00 | 5.00 |
| Calcium Pantothenate (solid) | 0.50 | 0.50 | 3.50 | 1.00 |
| Tocopherol Acetate | 0.50 | 0 | 0 | 0 |
| Fumed Silica | 0.18 | 0.18 | 0.18 | 0.18 |
| Dipropylene Glycol | 0.18 | 0.18 | 0.18 | 0.18 |
| Microthene | 0.18 | 0.18 | 0.18 | 0.18 |
| Behenyl Alcohol | 0.08 | 0.08 | 0.08 | 0.08 |
| Perfume | 0.75 | 0.75 | 0.75 | 0.75 |
| Cyclopentasiloxane | QS | QS | QS | QS |
| Total | 100.00 | 100.00 | 100.00 | 100.00 |

TABLE 3

Antiperspirant Low Sticks (Solid) Residue

| Ingredients | Example 3.1 | Example 3.2 | Example 3.3 | Example 3.4 |
|---|---|---|---|---|
| Al Zr Trichlorohydrex Glycinate (solid) | 25.25 | 20.00 | 20.00 | 20.00 |
| Dimethicone (50 cs) | 5.00 | 5.00 | 5.00 | 5.00 |
| Fully Hydrogenated High Erucic Acid Rapeseed oil (HEAR oil) | 15.00 | 15.00 | 15.00 | 15.00 |
| Isopar M | 10.00 | 10.00 | 10.00 | 10.00 |
| Niacinamide (solid) | 3.50 | 3.50 | 0 | 7.00 |
| C-18-36 Acid Triglyceride Syncrowax HGLC | 3.75 | 3.75 | 3.75 | 3.75 |
| Perfume | 0.75 | 0.75 | 0.75 | 0.75 |
| Calcium Pantothenate (solid) | 0.50 | 0.50 | 3.50 | 1.00 |
| Tocopherol Acetate | 0.50 | 0 | 0 | 0 |
| Cyclopentasiloxane | QS | QS | QS | QS |
| Total | 100 | 100 | 100 | 100 |

Example 4
Antiperspirant Aerosols

The Table 4 examples of aerosol embodiments can be prepared by methods well know for making aerosol antiperspirant products, such as those methods described in U.S. Pat. No. 6,136,303 (Ruebusch et al.); U.S. Pat. No. 4,904,463 (Johnson et al.) and U.S. Pat. No. 4,840,786 (Johnson et al.). The Table 4 examples can be prepared by combining the water-soluble solids (e.g., niacinamide, calcium pantothenate, etc.) with the solid antiperspirant active in an aerosol container. All other materials are mixed together to form a homogeneous premix liquid before adding the newly formed premix to the aerosol container. The propellant is then added, under pressure, and the container sealed.

TABLE 4

Antiperspirant Aerosols

| Ingredients | Example 4.1 | Example 4.2 | Example 4.3 | Example 4.4 |
|---|---|---|---|---|
| 5/6 Aluminum chlorohydrate solid (Macrospherical - 95) Reheis Chemical Company | 10.50 | 10.50 | 11.00 | 10.50 |
| SE76 Silicone Gum[1] | 5.00 | 5.00 | 5.00 | 5.00 |
| SWS 801[2] | 15.00 | 15.00 | 15.00 | 15.00 |
| Cyclomethicone[3] | 3.40 | 3.40 | 3.40 | 3.40 |
| Niacinamide (solid) | 1.00 | 1.00 | 0 | 0.50 |
| Calcium Pantothenate (solid) | 0.50 | 0.50 | 1.00 | 0.50 |
| Vitamin C (solid) | 0 | 0 | 0 | 0.50 |
| Tocopherol Acetate | 0.50 | 0 | 0 | 0.50 |
| Propellant A-46[4] | QS | QS | QS | QS |
| Total | 100.00 | 100.00 | 100.00 | 100.00 |

[1]Silicone gum pre-mix (15% silicone - 15 × 10$^6$ centipoise and 85% cyclomethicone); General Electric Company
[2]Diamino-functional silicone, m.w. 76,000; SWS Silicone, inc.
[3]Total cyclomethicone, including that contained in the silicone premix described in note 2.
[4]Mixture of 87% Isobutane and 13% propane (by weight of total propellant)

Example 5
Antiperspirant Liquids

The Table 5 examples are each prepared by combining and mixing together the various components under ambient conditions. Each of the resulting mixtures is then milled on a IKA brand T 25 Ultra-Turrax disperser (4 speed setting) using the S 25 N—25F attachment. The mixture is subjected to the milling process long enough to reduce and break up any water-soluble solids and or antiperspirant active agglomerates. The mixture is sufficiently milled when a small sample as examined under a polarizing microscope shows no visible agglomerates greater than 10 microns. Once milling is complete, the liquid antiperspirant product is poured into roll-on antiperspirant containers, or other suitable liquid antiperspirant dispenser.

TABLE 5

Antiperspirant Liquids

| Ingredients | Example 5.1 | Example 5.2 | Example 5.3 | Example 5.4 |
|---|---|---|---|---|
| Al Zr Trichlorohydrex Glycinate (solid) | 21.25 | 21.25 | 21.75 | 20.00 |
| Dimethicone (10 cs) | 10.00 | 10.00 | 10.00 | 10.00 |
| Microthene | 7.00 | 7.00 | 7.00 | 7.00 |
| Bentone 38 | 1.00 | 1.00 | 1.00 | 1.00 |
| Cab-O-Sil | 0.70 | 0.70 | 0.70 | 0.70 |
| Propylene Carbonate | 0.30 | 0.30 | 0.30 | 0.30 |
| Perfume | 0.50 | 0.50 | 0.50 | 0.50 |
| Niacinamide (solid) | 3.50 | 3.50 | 0 | 2.0 |
| Calcium Pantothenate (solid) | 0.50 | 0.50 | 3.50 | 1.0 |
| Vitamin C | 0 | 0 | 0 | 2.0 |
| Tocopherol Acetate | 0.50 | 0 | 0 | 0 |

TABLE 5-continued

Antiperspirant Liquids

| Ingredients | Example 5.1 | Example 5.2 | Example 5.3 | Example 5.4 |
|---|---|---|---|---|
| Cyclopentasiloxane | QS | QS | QS | QS |
| Total | 100.00 | 100.00 | 100.00 | 100.00 |

Example 6
Deodorants

The Table 6 examples are each prepared by combining and mixing together the deodorant and skin active solid (e.g., calcium pantothenate, niacinamide, etc.) in an aerosol container. The silicone gum, amino-functionalized silicone, cyclomethicone and fragrance are premixed and added to the can. The propellant is then added, under pressure, and the can sealed. These formulations can be prepared by methods well known in the antiperspirant art, a non-limiting example of which is described in U.S. Pat. No. 4,806,338 (Luebbe et al.), which description is incorporated herein by reference.

TABLE 6

Deoderants

| Ingredients | Example 6.1 | Example 6.2 | Example 6.3 | Example 6.4 |
|---|---|---|---|---|
| Triclosan | 0.3 | 0.3% | 0.3% | 0 |
| Sensiva SC-50[1] | 0 | 0 | 0.6% | 0.6% |
| SE76 Silicone Gum[2] | 5.00 | 5.00 | 5.00 | 5.00 |
| SWS 801[3] | 15.00 | 15.00 | 15.00 | 15.00 |
| Cyclomethicone[4] | 3.40 | 3.40 | 3.40 | 3.40 |
| Niacinamide (solid) | 1.00 | 1.00 | 0 | 0.50 |
| Calcium Pantothenate (solid) | 0.50 | 0.50 | 1.00 | 0.50 |
| Vitamin C (solid) | 0 | 0 | 0 | 0.50 |
| Tocopherol Acetate | 0.50 | 0 | 0 | 0.50 |
| Perfume | 3.0 | 2.0 | 2.0 | 2.0 |
| Propellant A-46[5] | QS | QS | QS | QS |
| Total | 100.00 | 100.00 | 100.00 | 100.00 |

[1]A synthetic representative of the 1-alkyl glycerin ethers with a high degree of purity; mfr. S.A Schulke & Mayr, Belgium N.V.
[2]Silicone gum pre-mix (15% silicone - 15 × 10$^6$ centipoise and 85% cylomethicone); General Electric Company
[3]Diamino-functional silicone, m.w. 76,000; SWS Silicone, inc.
[4]Total cyclomethicone, including that contained in the silicone premix described in note 2.
[5]Mixture of 87% Isobutane and 13% propane (by weight of total propellant)

What is claimed is:

1. Anhydrous antiperspirant and deodorant compositions comprising:
   (a) from about 0.1% to about 30% by weight of an underarm active;
   (b) from about 0.01% to about 10% by weight of a solid, water-soluble, d-pantothenate salt;
   (c) from about 0.1% to about 40% by weight of a suspending agent; and
   (d) from about 10% to about 99% by weight of an anhydrous carrier liquid.

2. An anhydrous composition according to claim 1, wherein the d-pantothenate salt is selected from the group consisting of calcium salts, sodium salts, potassium salts, magnesium salts, zinc salts, and combinations thereof.

3. An anhydrous composition according to claim 1, wherein the d-pantothenate salt is calcium pantothenate.

4. An anhydrous composition according to claim 2, wherein the d-pantothenate salt represents from about 0.1% to about 5%, by weight of the composition.

5. An anhydrous composition according to claim 2, wherein the composition contains less than 1% by weight of free or added water.

6. An anhydrous composition according to claim 2, wherein the underarm active comprises a solid antiperspirant active selected from the group consisting of zirconium-containing active, aluminum-containing active, and combinations thereof, and wherein the solid antiperspirant active represents from about 5% to about 30% by weight of the anhydrous composition.

7. An anhydrous composition according to claim 2, wherein the underarm active comprises an antimicrobial deodorant active, and wherein the antimicrobial deodorant active represents from about 0.1% to about 5% by weight of the composition.

8. An anhydrous composition according to claim 2, wherein the antimicrobial active is selected from the group consisting of triclosan, triclocarban, and combinations thereof.

9. An anhydrous composition according to claim 2, wherein the anhydrous carrier comprises a volatile cyclomethicone that represents from about 5% to about 80% by weight of the composition.

10. An anhydrous composition according to claim 9, wherein the anhydrous carrier further comprises a non-volatile silicone liquid that represents from about 1% to about 35% by weight of the composition.

11. An anhydrous antiperspirant composition according to claim 2, wherein the average particle diameter of the d-pantothenate salt particulates is from about 3 $\mu$m to about 100 $\mu$m.

12. An anhydrous antiperspirant composition according to claim 2, wherein the average particle diameter of the d-pantothenate salt particulates is from about 5 $\mu$m to about 40 $\mu$m.

13. A method of controlling underarm perspiration wetness or odor, said method comprising the topical application to the underarm of from about 0.1 grams to about 20 grams per underarm of a composition according to claim 2.

14. A method according to claim 13, wherein the composition is applied to a shaven underarm.

15. A method of making anhydrous antiperspirant and deodorant compositions, said method comprising the steps of
   (a) preparing an intermediate composition by mixing together the following components:
      (i) from about 0.1% to about 30% by weight of a solid, antiperspirant or deodorant active;
      (ii) from about 0.01% to about 20% by weight of a solid, pantothenate salt;
      (iii) from about 0.1% to about 40% by weight of a suspending agent; and
      (iv) from about 10% to about 99% by weight of an anhydrous carrier liquid that is substantially free of nonvolatile organic liquids having a C log P value greater than about 7.0;
   (b) heating the intermediated composition to form a liquid intermediate composition containing solid antiperspirant active and solid, water-soluble, skin active agent, and solid aggregates thereof;
   (c) milling the liquid intermediate composition for a period of time sufficient to reduce the average particle diameter of the solid aggregates to less than 50 $\mu$m; and then (d) pouring the milled liquid intermediate into a dispensing package and allowing the packaged composition to cool to ambient temperatures, to form an anhydrous antiperspirant and deodorant composition.

16. The method of claim 15, wherein the solid d-pantothenate salt is selected from the group consisting of calcium salts, sodium salts, potassium salts, magnesium salts, zinc salts, and combinations thereof.

17. The method of claim 16, wherein the solid d-pantothenate salt comprises calcium pantothenate, and wherein the calcium pantothenate salt represents from about 0.1% to about 5%, by weight of the composition.

18. The method of claim 17, wherein the anhydrous antiperspirant and deodorant composition contains less than about 1% by weight of free or added water.

19. The method of claim 18 wherein the antiperspirant or deodorant active is selected from the group consisting of aluminum chlorohydrate, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum zirconium trichlorohydrate, aluminum zirconium tetrachlorohydrate, aluminum zirconium pentatchlorohydrate, aluminum zirconium octachlorohydrate, aluminum zirconium trichlorohydrex glycine complex, aluminum zirconium tetrachlorohydrex glycine complex, aluminum zirconium pentachlorohydrex glycine complex, aluminum zirconium octachlorohydrex glycine complex, aluminum chloride, aluminum sulfate buffered, and combinations thereof.

* * * * *